US010849571B2

(12) United States Patent
Trindade Rodrigues et al.

(10) Patent No.: US 10,849,571 B2
(45) Date of Patent: Dec. 1, 2020

(54) DETERMINING STANDARD UPTAKE VALUE (SUV) IN EMISSION TOMOGRAPHY IMAGING USING SUV-RELATED DATA AND EVENT DATA

(71) Applicant: KONINKLIJKE PHILIPS N.V., Eindhoven (NL)

(72) Inventors: Andreia Maria Araujo Trindade Rodrigues, Veldhoven (NL); Pedro Jorge Da Silva Rodrigues, Veldhoven (NL); Andreas Goedicke, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 291 days.

(21) Appl. No.: 15/766,861

(22) PCT Filed: Oct. 21, 2016

(86) PCT No.: PCT/EP2016/075302
§ 371 (c)(1),
(2) Date: Apr. 9, 2018

(87) PCT Pub. No.: WO2017/072030
PCT Pub. Date: May 4, 2017

(65) Prior Publication Data
US 2018/0289340 A1    Oct. 11, 2018

(30) Foreign Application Priority Data
Oct. 28, 2015  (EP) ...................................... 15191876

(51) Int. Cl.
*A61B 6/03* (2006.01)
*A61B 5/11* (2006.01)
(Continued)

(52) U.S. Cl.
CPC .......... *A61B 6/037* (2013.01); *A61B 5/02416* (2013.01); *A61B 5/02438* (2013.01);
(Continued)

(58) Field of Classification Search
None
See application file for complete search history.

(56) References Cited

U.S. PATENT DOCUMENTS 9,606,245 B1 * 3/2017 Czarnecki ............. G01T 1/2006
2009/0304582 A1   12/2009 Rousso
(Continued)

FOREIGN PATENT DOCUMENTS

JP    2007333471    12/2007
WO    2006/129301    12/2006

OTHER PUBLICATIONS

Boellaard, "Standards for PET Image Acquisition and Quantitative Data Analysis", J Nucl Med 2009, 50:11S-20S.
(Continued)

*Primary Examiner* — Tahmina N Ansari

(57) ABSTRACT

The invention relates to a device (40) for standard uptake value, SUV, determination during an emission tomography imaging procedure of a patient. The device receives SUV-related data required for SUV determination, and event data relating to one or more events that may affect the SUV determination. The SUV-related data includes a time of administration of the radiotracer dose to the patient. The event data includes at least one of: a time at which an emission tomography imaging procedure of the patient is performed, patient motion data, patient position data, and patient vital signs data. An anomalous event determination unit (42) determines, based on the event data, anomalous event information indicative of one or more anomalous events that affect the SUV determination. An SUV determi-
(Continued)

nation unit (43) determines the SUV based on said SUV-related data taking into account the anomalous event information.

17 Claims, 4 Drawing Sheets

(51) Int. Cl.
*A61B 6/00* (2006.01)
*A61B 5/024* (2006.01)
*A61B 5/00* (2006.01)
*G16H 10/60* (2018.01)
*G16H 40/63* (2018.01)

(52) U.S. Cl.
CPC ........... *A61B 5/1114* (2013.01); *A61B 5/1118* (2013.01); *A61B 5/681* (2013.01); *A61B 6/4258* (2013.01); *A61B 6/467* (2013.01); *A61B 6/545* (2013.01); *A61B 6/56* (2013.01); *G16H 10/60* (2018.01); *G16H 40/63* (2018.01)

(56) References Cited

U.S. PATENT DOCUMENTS

| | | |
|---|---|---|
| 2011/0112856 A1 | 5/2011 | Rousso |
| 2013/0131422 A1* | 5/2013 | Vosniak .................. A61B 6/037 600/1 |
| 2013/0225950 A1 | 8/2013 | Van Elswijk |
| 2014/0312242 A1 | 10/2014 | Valentino |
| 2017/0119273 A1* | 5/2017 | Thakur .................. A61B 5/046 |
| 2018/0008204 A1* | 1/2018 | An .................... H04W 52/0229 |
| 2018/0289340 A1* | 10/2018 | Trindade Rodrigues .................... A61B 5/1118 |

OTHER PUBLICATIONS

"ZWear—A wearable platform for makers", http://zwear.org/; Product page reference, 2014.

"FDG-PET/CT as an Imaging Biomarker Measuring Response to Cancer Therapy"; Quantitative Imaging Biomarkers Alliance, FDG-PET/CT Technical Committee, Version 1.05, Publicly Reviewed Version. QIBA, Dec. 11, 2013, Available from: rsna.org/qiba.

* cited by examiner

DETERMINING STANDARD UPTAKE VALUE (SUV) IN EMISSION TOMOGRAPHY IMAGING USING SUV-RELATED DATA AND EVENT DATA

CROSS REFERENCE TO RELATED APPLICATIONS

This application is the U.S. National Phase application under 35 U.S.C. § 371 of International Application No. PCT/EP2016/075302, filed Oct. 21, 2016, published as WO 2017/072030 on May 4, 2017, which claims the benefit of European Patent Application Number 15191876.0 filed Oct. 28, 2015. These applications are hereby incorporated by reference herein.

FIELD OF THE INVENTION

The present invention relates to a device and method for standard uptake value (SUV) determination in emission tomography, such as particle emission tomography (PET) or single-photon emission computed tomography (SPECT). The present invention relates further to an emission tomography system, such as a PET or SPECT system, and to a wearable device configured to be worn by a person (e.g. the patient, a technologist, supporting clinical staff that escorts the patient, and/or a care giver), in particular for use in such an emission tomography system.

BACKGROUND OF THE INVENTION

Positron Emission Tomography (PET) is a medical imaging modality that allows extracting quantitative information about bio distribution of metabolic active contrast agents, e.g. FDG, FET, FLT, FMISO, etc. PET not only allows visually representing the distribution of administered, metabolically active radiopharmaceuticals, but it also allows quantifying how much of the radiopharmaceutical (also called radiotracer herein) has accumulated within a specific region. For instance, administrating FDG (a glucose analogue) allows quantifying the cell inwards glucose transport, as FDG is trapped inside the cells. Tumor cells are highly metabolically active and uptake and retain higher levels of FDG when compared to normal tissues. With PET it is possible to tell exactly how many decays from the radio isotope were counted in the specific region. This makes it possible to compare these numbers to a previous or later PET scan and evaluate, if the uptake and retention has remained stable, decreased or increased. This evaluation is of utmost importance for evaluation if a disease responds to a therapy, especially in oncology.

For practical ease, Standard Uptake Values (SUV) are computed in clinical routine instead of directly using decay counts. The SUV is used for quantifying the relative average activity and the relative maximum activity of lesions. A correct computation of SUV values is especially important for evaluation of tumors to therapy. Several evaluation criteria exist, such as RECIST, PERCIST, EORTC, WHO, wherein the evaluation criteria PERCIST and EORTC evaluate the SUV values in treated tumors. These schemes indicate how to interpret quantitative PET images for deciding if a cancer responds to a therapy or not, e.g. the EORTC criteria recommends to classify a cancer disease as progressive if the SUV increases by more than 15% from one PET scan to a second one. An improved computation of SUV values thus leads to improved evaluation of the disease.

For this purpose, a reconstructed PET image is converted to absolute activity of the administered radiopharmaceutical in each image pixel. The advantage of this form of interpreting PET images is that it allows comparing clinically suspicious tracer accumulation in organs or parts of the body at different point in time in order to forecast evolution or response to treatment. PET quantitation can however be hampered by several factors. To minimize the impact of this factors and the associated source of errors several standards have been defined, which define guidelines of good practice. The SUV value is computed for each PET image pixel. For better characterization, normally the maximum value (SUV-max) of a determined region of interest (ROI) and the mean value (SUVmean) of a determined ROI are reported.

Three factors are generally relevant for the SUV computation, namely concentration of the radiotracer in the tissue, injected dose, and patient weight. While the concentration of the radiotracer in the tissue is generally extracted from the reconstructed image, patient weight and injected dose have to be provided by the clinicians. Alternative ways to compute the SUV rely also on patient height or total body surface area. For determination of the injected dose, the charged syringe is located in a dose calibrator. The clinician then has to write down the dose, type it into a mask for the patient and image information, together with the exact time of measurement. Ideally, these steps are repeated after injection of the radiotracer to estimate the residual dose in the syringe. All these steps are cumbersome and error prone, particularly due to the generally high workload of the clinical staff. Patient comfort is also a key driver since patient stress and poor waiting conditions result in uptake of the radiotracer (e.g. FDG) in muscle or brown fat and therefore affect SUV quantification.

This results in several main factors that affect the SUV computation, namely relative calibration between PET and dose calibrator, residual activity in syringe/administration system, incorrect clock synchronization between PET and dose calibrator, injection vs. calibration time, incorrect recording of the patient weight and height, and patient comfort.

US 2011/112856 A1 discloses a method for managing a plurality of medical imaging procedures. The method comprises associating a machine readable tag with each of a plurality of patients designated for a plurality of medical imaging procedures, monitoring a progress of at least one of the plurality of patients in a respective the medical imaging procedure, and managing at least one medical imaging resource for performing the plurality of medical imaging procedures according to the progress.

US20130131422A1 discloses various systems and methods for communicating dose calibration information. One method includes determining dose calibration information of a radiopharmaceutical at a dose calibrator. The method also includes automatically storing the dose calibration information in a memory. The method further includes communicating the stored dose calibration information to a host system.

SUMMARY OF THE INVENTION

It is an object of the present invention to provide a device and method for SUV determination in emission tomography, by which the SUV determination is more accurate, less cumbersome (in particular for the clinical staff), more comfortable for the patient and less error-prone.

It is a further object of the present invention to provide a corresponding emission tomography system and a wearable device, in particular for use in such an emission tomography system, that enable the achievement of such advantages in the SUV determination.

In a first aspect of the present invention a device for SUV determination in emission tomography is presented comprising:

an input for obtaining, from one or more wearable devices and/or one or more biometrical data acquisition units, SUV-related data required for SUV determination including the time of a radiotracer uptake by a patient, and for obtaining event data relating to one or more events that may affect the SUV determination, an anomalous event determination unit configured to determine from the obtained event data anomalous event information indicating one or more anomalous events that affect the SUV determination, and an SUV determination unit configured to determine the SUV from said SUV-related data taking into account the anomalous event information.

In a further aspect of the present invention a wearable device configured to be worn by a patient is presented comprising a holding element for holding the wearable device at the patient's body, one or more sensing elements for sensing standard uptake value, SUV, related data required for SUV determination in emission tomography, including the time of a radiotracer uptake by the patient, and event data relating to one or more events that may affect the SUV determination, and an output for outputting the sensed SUV-related data and event data.

In a further aspect of the present invention an emission tomography system is presented comprising an imaging arrangement for acquiring image data of a patient, one or more biometrical data acquisition units for acquiring biometrical data, in particular a weighing scale, a height measuring scale, a blood pressure meter, and/or a blood glucose analyzer, and for providing said biometrical data to one or more wearable devices.

a device for standard uptake value, SUV, determination as claimed in claim 1 from SUV-related data and event data obtained from the one or more wearable devices and/or the one or more biometrical data acquisition units, and an evaluation unit for evaluating the acquired image data using the determined SUV.

In yet a further aspect of the present invention a corresponding method for SUV determination is presented.

In yet further aspects of the present invention, there are provided a computer program which comprises program code means for causing a computer to perform the steps of the method disclosed herein when said computer program is carried out on a computer as well as a non-transitory computer-readable recording medium that stores therein a computer program product, which, when executed by a processor, causes the method disclosed herein to be performed.

Preferred embodiments of the invention are defined in the dependent claims. It shall be understood that the claimed method, system, computer program and medium have similar and/or identical preferred embodiments as the claimed device and the claimed wearable device, in particular as defined in the dependent claims and as disclosed herein.

As explained above, the conventional workflow for quantitative PET is quite cumbersome and error prone. Wrongly computed SUV values are often obtained due to mistakes in one of the following workflow steps: weighing the patient and inserting value into a steering imaging system control console, measuring the radiation dose, registering the measurement time, registering the injection time, and registering the residual radiation dose. An error in one of these steps is often made due to high workload of the clinical staff and leads to wrong SUV values. Automating these steps, as proposed by the present invention, leads to more reliable SUV values and to an easier and faster workflow and thus to an increased patient throughput and improved return on investment for the operator of the emission tomography system, such as a PET or SPECT system.

Further, patient comfort is increased by the present invention since patient stress and poor waiting conditions result in uptake of the radiotracer in muscle or brown fat and therefore disadvantageously affect the SUV quantification. However, patient stress that usually involves muscular tension is conventionally undetected and only shows up during the image reconstruction process. By use of the present invention this can be detected and improved.

According to an element of the present invention an integrated hardware solution is proposed that records the time of occurrence of at least the time of a radiotracer uptake by the patient, which is one piece of SUV-related data required for SUV determination. Further, event data relating to one or more events that may affect the SUV determination are recorded, including e.g. different time events, from patient preparation, resting and actual examination. The patient wears a wearable device, preferably loaded with a software app, which is able to sense and record the different events, preferably together with the time of occurrence of the respective event. The software app may also be able to process digital information from intelligent weight and height scales, blood pressure and glucose analyzers. These data are then processed to determine the SUV.

Particularly, anomalous event information indicating one or more anomalous events that affect the SUV determination is determined according to the present invention. "Anomalous" in this context means that an event may be such that its occurrence, its time of occurrence, its strength of occurrence, or any other characteristic of the event has an influence on the determination of the SUV.

In an embodiment said SUV determination unit is configured to determine the SUV from SUV-related data including the radiotracer activity concentration in the patient's tissue, the administered dose of the radiotracer uptake and the patient's biometrical data, in particular the patient's weight, height and/or total surface area. These data may be obtained automatically from other connected devices (biometrical data acquisitions units, e.g. an intelligent weight scale or height scale) and/or via input (from the user or the patient), e.g. into the wearable device, or may be retrieved from a central storage, such as the record of the patient stored in a hospital's central database, e.g. the electronic health record of the patient.

For this purpose, the device may further comprise an interface for interconnecting with a radiotracer dose calibrator, a radiotracer dose injector, one or more biometrical data acquisition units, in particular a weighing scale, a height measuring scale, a blood pressure meter, and/or a blood glucose analyzer, and/or an imaging arrangement to obtain one or more pieces of SUV-related data including the radiotracer activity concentration of the patient's tissue, the administered dose of the radiotracer uptake and the patient's biometrical data.

In another embodiment said input is further configured to obtain event data including the time of the one or more events and said anomalous event determination unit is configured to use the time of the one or more events in determining the anomalous event information.

According to a further embodiment the proposed device further comprises a synchronization unit for time synchronization of the device with the one or more wearable devices and/or the one or more biometrical data acquisition units, in particular for generating a system clock provided to the one or more wearable devices and/or the one or more biometrical data acquisition units. Preferably, all components of the proposed system, such as a central computer of the system or the imaging device, are synchronized. For instance, all clocks in an imaging facility used to record activity/injection measurements may be synchronized to standard time reference within +/−1 second. These include any clocks or timekeeping systems that are connected with a subject's study, in particular those associated with a radionuclide calibrator, an injection room, an imaging scanner, and acquisition computer(s). Further, the wearable device is preferably kept synchronized with the remaining elements of the system, such as the dose calibrator, injector and imaging device. In an embodiment, the time of occurrence of each event is transmitted by the wearable device to a master logger which routes the information to the imaging device control console. For every examination these parameters may then be stored and can be monitored either in real-time or after the examination.

For collecting information for use in the SUV determination a wearable device that can be worn by the patient is proposed. Generally, it can have any form and can be worn at any body part, but preferably it has the form of a wrist-worn device, wherein the holding element is a wrist band. Other embodiments may e.g. be a body worn device, such as a device worn like a belt or a necklace. In an embodiment, for frail patients with poor health conditions the wearable device is carried by a technologist, care giver or supporting clinical staff that escorts the patient.

The wearable device generally comprises one or more sensing elements for sensing SUV-related data and event data relating to one or more events that may affect the SUV determination. Such sensing elements may generally have different forms and/or functions and may include one or more of a motion sensor, an accelerometer, a position detection sensor, a vital sign sensor (e.g. a heart beat sensor, a temperature sensor, a respiration sensor, a blood pressure sensor, a skin conductivity sensor, an SpO2 sensor, etc.), a gamma radiation sensor, a camera, or any other sensing element that may be used to acquire data or monitor the quality of the data use in the SUV determination.

The wearable device may further comprise a time measurement unit for recording the time of occurrence of the one or more events sensed as event data, wherein said output is configured to output the event data together with the time of occurrence of the related event. It has been found that the time at which SUV-related events occur play an important role in the determination of the SUV.

As mentioned above with respect to the device for SUV determination, time synchronization of all elements of the system is preferred. Hence, in an embodiment the wearable device may further comprise a synchronization unit for time synchronization of the wearable device with a device for SUV determination as disclosed herein, in particular based on a provided system clock generated and distributed e.g. by a master clock unit.

The wearable device may further comprise a user interface enabling input and/or output of user information. For instance, the user (who may also be the patient) can e.g. enter data relevant for SUV determination, such as his weight, or may enter event data (e.g. there may be a button to confirm certain events (e.g. injection of radiotracer) in response to which the time of this event is automatically recorded). Further, information may be provided to the user, such as the remaining waiting time, request to the user what he should do, etc.

The data used for the SUV determination may generally be provided by the one or more wearable devices worn by the patient. However, some of these data may also be obtained in another way, e.g. via input at a user interface of a wearable device or at the SUV determination device or in (wired or wireless) transmission manner from one or more additional sensors, as proposed in an embodiment, for sensing one or more event data. For example patient's biometrical data acquisition units (e.g. a weighing scale, height measuring scale, blood pressure, blood glucose analyzer) relevant for the SUV calculation or quality assessment can be used to acquire and transmit biometrical data of the patient to the wearable in a digital form.

The device for SUV determination may further be configured to additionally use the one or more event data sensed by one or more additional sensors in the SUV determination. Such additional sensors may e.g. include one or more cameras for monitoring the patient, e.g. while he is walking around to recognize if he e.g. uses the toilette or moves fast, etc. Further, sensors for monitoring the passing of a person may be used. Still further, conventional body-worn sensors, such as a conventional heart rate sensor or SpO2 sensor, or a camera configured for remote photoplethysmography may be used for acquiring one or more vital signs.

In an embodiment the wearable device may be considered as a mobile patient tracking device (also called nuclear medicine (NM) tracker or NMT) equipped with a unique assembly of sensors tailored to support the workflow specific data logging and communication tasks. The NMT is preferably assigned and handed out to the patient (e.g. during its registration procedure), and accompanies him until he leaves the department again. As mentioned above it may offer a simple user interface e.g. to display procedure related information to the patient. Using the inbuilt gamma radiation sensor, the device automatically detects a radiotracer injection event. Further workflow related information is captured during the procedure, e.g. via a (near-field) RF-interface and/or the inbuilt camera (e.g. in combination with QR-tag or OCR technology). Via e.g. the existing wireless network in the clinic, the NMT communicates with a central base station, representing the SUV determination device, to transfer collected path (motion) tracking information and recorded technical and physiological parameters. An application running on the SUV determination device (which may also be implemented as a kind of server or base station) may then analyze the incoming data, check it for workflow state consistency, and/or raise warnings to the medical staff in case of any undesirable events. It may furthermore offer an interface to submit further information to the remotely connected NMTs.

Preferably, the wearable device further comprises a communication unit for electronically exchanging data with one or more biometrical data acquisition units, e.g. using a WLAN, Bluetooth, mobile communication, or any other (preferably wireless) communication means.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
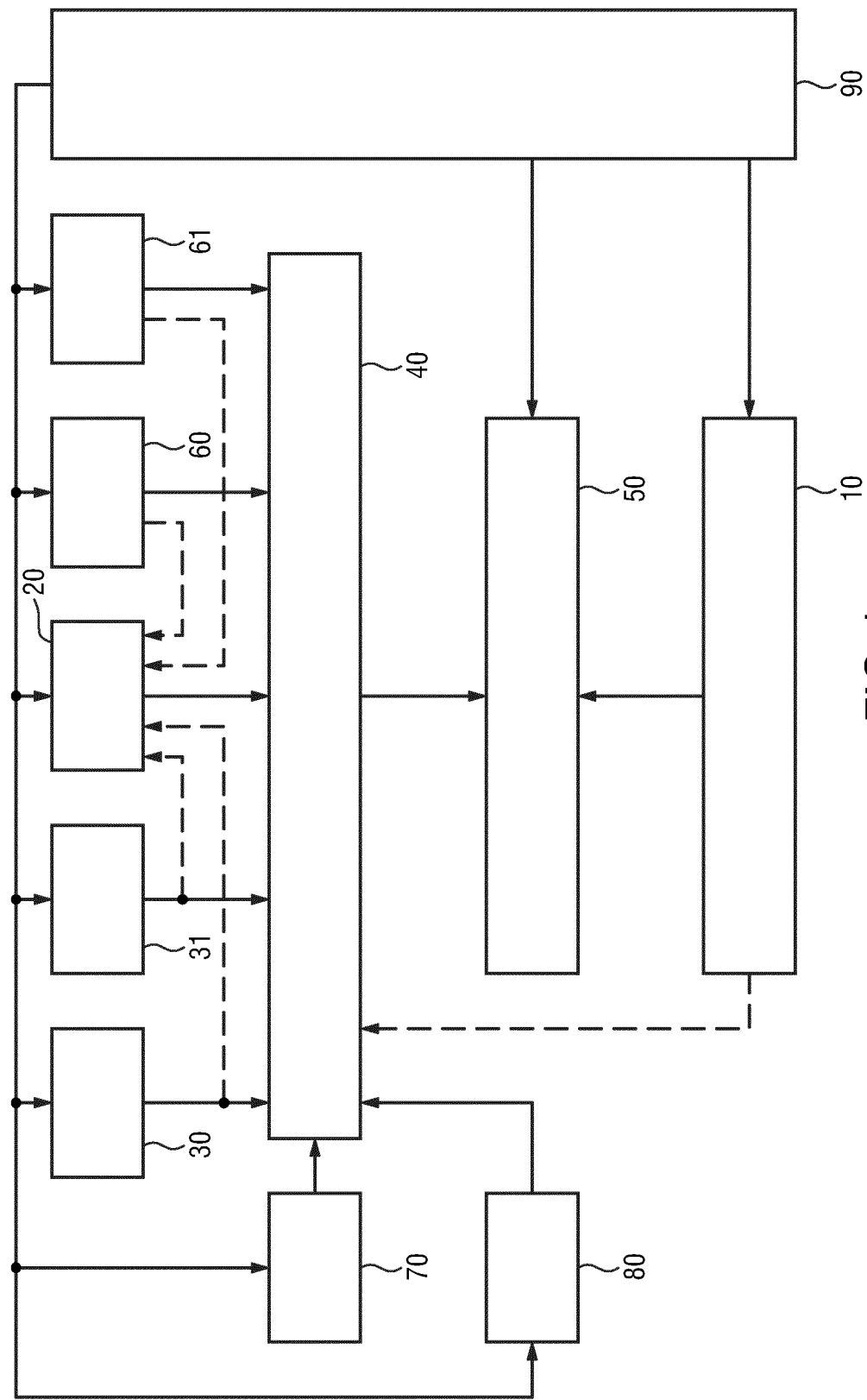
FIG. 1 shows a schematic diagram of an embodiment of an emission tomography system according to the present invention.

Nuclear medicine (NM) imaging non-invasively provides functional information at the molecular and cellular level that contributes to the determination of health status by measuring the uptake and turnover of target-specific radiotracers in tissue. Radiation emitted from the decay of the administered radioisotope is detected using body-external sensors. In SPECT these detectors (gamma cameras) rotate on a gantry around the patient, while in PET a static ring detector setup is typically used to map the emitted radiation pattern. Transformed back into a visual 2D or 3D representation of the body-internal radiotracer distribution, spotted non-physiological tracer accumulations are further evaluated by the clinician for their significance in indicating ongoing disease specific processes. For certain clinical applications and disease monitoring, e.g. under treatment, this qualitative assessment of reconstructed image data is increasingly extended by a quantitative analysis of the local radiotracer density. Thereby, changes in the underlying cellular-processes can often be (much) earlier discovered than macroscopic changes in the tissue. Even if e.g. a tumor lesion does not immediately change in size, a significant effect on e.g. the local metabolism or signaling rate under treatment may early indicate a related response.

Accurate quantitative NM data assessment requires to strictly follow predefined workflow steps. Mandatory regular quality assurance procedures have to be performed and documented for each device. Isotope specific calibration factors have to be determined for each individual scanner, to enable converting reconstructed image intensities into activity values. Various physiological parameters have to be collected (e.g. for PET: glucose, Creatinine, TSH, BP, patient weight) together with time-stamped information on the radiotracer activity actually administered to the patient. Begin and duration of the data acquisition have to be logged, as well as the setup for any subsequent post-processing steps applied to reconstruct the final image and extract the regional quantity of interest. This complex procedure and information handling makes quantitative data assessment fault-prone, resulting in a non-optimal outcome fluctuation, especially in multi-center studies but also in single-center trials.

According to the binding and decay properties of the applied ligand-radioisotope combination, the imaging workflow requires a delay between the tracer administration and the start of the imaging procedure (typically 45-60 minutes). For time-optimized employment of the NM scanner equipment, patients are pre-examined, injected and asked to stay in the waiting zone during the data acquisition of other patients.

Proper intra-venous injection of the prepared radiotracer is key for any following step. The clinician has to make sure that the radiotracer does not accidentally stay in the tissue at the injection site and has to record the injection time, as optimal patient/study management recommends starting the image acquisition within a fixed, time frame after injection. However, besides standard-techniques for drug injection, there is currently no system and device supporting to automatically perform this logging procedure based on a detected radiotracer bolus.

Especially for PET, the patients in waiting should diminish muscular activities (e.g. walking around) to avoid related physiological tracer accumulation. Any relevant deviations from recommendations should be recorded to consider this behavior during the data analysis. However, clinical staffing situation typically does not allow for such a personalized monitoring which could technical be easily achieved.

Further, before the acquisition starts, the patient is generally asked to empty his/her bladder, in order to avoid high local activity related imaging artifacts and the risk of sudden urge to urinate during the scan as well as to reduce the bladder dose. However, quite often it is noted that the patient did not yet follow this explicit advice, which then leads to an unfavorable delay (for the current and following scans), especially in elderly and less mobile patients. These (accumulating) delays could be reduced via a mobile monitoring device capable to log (and remotely indicating to the medical staff) the patients latest bathroom visit.

In case of a delay (e.g. when additional scans have to be performed to further consolidate a suspected diagnosis), later scheduled and not yet prepared/injected patients are allowed to spend their waiting time outside the department. However, as the private communication (e.g. via private mobile phones) is normally restricted or even technically prohibited inside a hospital area, easy on-demand recalling of the patient is currently not supported. As a consequence, patients often have to stay in the department's waiting zone. Establishing a (confirmed) signaling between the patient and the department regarding e.g. the (new) preparation/acquisition time could be easily provided using a mobile patient tracking device.

One or more of the above discussed issues are addressed by the present invention. FIG. 1 shows a schematic diagram of an embodiment of an emission tomography system 1 according to the present invention. The system may e.g. be a PET system, a SPECT system, or a combined PET/SPECT, PET/MR, PET/CT or SPECT/CT system for acquiring medical images of a patient.

The system 1 comprises an imaging arrangement 10 for acquiring image data of a patient. Said imaging arrangement 10 may e.g. be a conventional PET imaging or SPECT imaging unit comprising a gantry and a gamma detector, and optionally an x-ray imaging system or a CT imaging system.

The system 1 further comprises one or more wearable devices 20 configured to be worn by the patient (or by a person accompanying the person, such as a care giver). The wearable device 20, which may e.g. be configured to be worn like a wristwatch, is configured to acquire SUV-related data required for SUV determination and event data relating to one or more events that may affect the SUV determination. Embodiments of such a wearable device 20 will be explained in more detail below. It may also be possible that a patient wears not only a single wearable device, but two or more (preferably different) wearable devices for obtaining different kinds of data.

The system 1 preferably further comprises one or more biometrical data acquisition units 30, 31 for acquiring biometrical data. Such units may include, but are not limited to, one or more of a weighing scale for acquiring the patient's weight, a height measuring scale for measuring the patient's height, a blood pressure meter for measuring the patient's blood pressure, and/or a blood glucose analyzer for analyzing the patient's glucose level.

The system 1 further comprises a device 40 for SUV determination from SUV-related data and event data obtained from the one or more wearable devices 20 and/or the one or more biometrical data acquisition units 30, 31. Such a device 40 may be implemented by use of hardware, software or a combination of hard- and software. A particular implementation uses an appropriately programmed processor or computer. Embodiments of such a device 40 will be explained in more detail below.

The system 1 further comprises an evaluation unit 50 for evaluating the acquired image data using the determined SUV. The evaluation unit 50 may also be implemented by use of hardware, software or a combination of hard- and software. A particular implementation uses an appropriately programmed processor or computer, e.g. the same processor or computer as used for implementing the device 40. For instance, a workstation used for image reconstruction of the medical images from the data acquired by the image data of the patient by the imaging arrangement 10 may also be used for implementing the device 40 and the evaluation unit 50.

The system 1 may further comprise one or more additional sensors 60, 61 for sensing one or more event data, which are then used by the device 40 for SUV determination in the SUV determination. Such additional sensors may include, but are not limited to, a movement sensor 60 carried by the patient (e.g. a GPS sensor or an indoor navigation sensor, which may be implemented in the wrist worn device) for recording movement and/or physical activity of the patient and/or the location of the patient, or a camera 61 for the same purpose. Other sensors may include passage sensors provided at doors to record if the patient passes through said door including a recording of the time of stay in the room. A reader may be provided to recognize the patient, e.g. from a tag worn by patient, or from other characteristic features of the patient (e.g. using face recognition, voice recognition, etc.).

The system 1 may further comprise a radiotracer dose calibrator 70 for determination of the activity and/or volume activity of the radiotracer and/or a radiotracer dose injector 80 for automatic injection (e.g. intravenous infusion) of the radiotracer.

The system 1 may further comprise a synchronization device 90 for time synchronization of the components of the system 1.

The imaging arrangement 10 may also be used to obtain one or more pieces of SUV-related data, such as the radiotracer activity concentration of the patient's tissue, the administered dose of the radiotracer uptake and the patient's biometrical data.

The components of the system 1 are preferably configured to provide acquired data to other components, e.g. to the SUV determination device 40 and/or the evaluation unit 50, as required to perform its function by the respective device. For instance, the biometrical data acquired by the biometrical data acquisition unit 30, 31 are provided to the wearable device 20, preferably through wireless transmission (e.g. via Wi-Fi, Bluetooth, mobile communication or a hospital network). Also the other components are preferably configured for wireless (or wired) transmission and/or reception of data.

Figure 2:
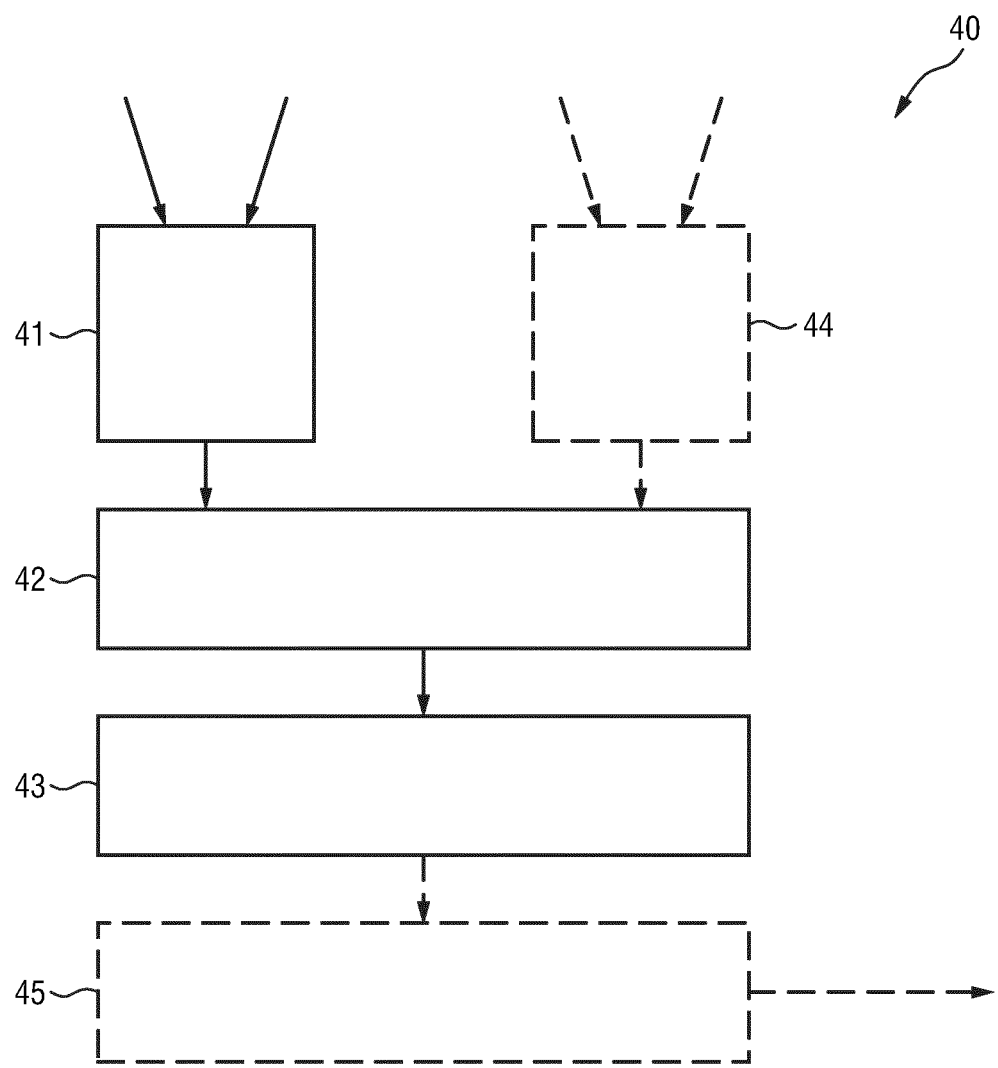
FIG. 2 shows a schematic diagram of an embodiment of a device for SUV determination according to the present invention.

FIG. 2 shows a schematic diagram of an embodiment of a device 40 for SUV determination according to the present invention. The device 40 comprises an input 41 for obtaining, from one or more wearable devices 20 and/or one or more biometrical data acquisition units 30, 31, e.g. worn by a patient or by a technologist, care giver or supporting clinical staff, SUV-related data required for SUV determination. Said SUV-related data particularly include the time of a radiotracer uptake by the patient. Further, event data relating to one or more events that may affect the SUV determination are obtained, particularly from the wearable device 20 and/or one or more biometrical data acquisition units 30, 31 and/or one or more additional sensors 60, 61. The input 41 may e.g. be implemented as a data interface for wireless or wired reception or retrieval of data from other components.

The device 40 further comprises an anomalous event determination unit 42 configured to determine from the obtained event data anomalous event information indicating one or more anomalous events that affect the SUV determination and an SUV determination unit 43 configured to determine the SUV from said SUV-related data taking into account the anomalous event information. The anomalous event determination unit 42 may e.g. be implemented as a processing unit or algorithm programmed on processor or computer. Hereby, "anomalous" shall be understood such that the occurrence, the time of occurrence, the strength of occurrence, or any other characteristic of an event has an influence on the determination of the SUV.

The SUV determination unit 43 may be configured to determine the SUV from SUV-related data including the radiotracer activity concentration in the patient's tissue, the administered dose of the radiotracer uptake and the patient's biometrical data, in particular the patient's weight, height and/or total surface area.

The device 40 may further comprise an interface 44 for interconnecting with a radiotracer dose calibrator 70, a radiotracer dose injector 80, one or more biometrical data acquisition units 30, 31 and/or an imaging arrangement 10 to obtain one or more pieces of SUV-related data including the radiotracer activity concentration of the patient's tissue, the administered dose of the radiotracer uptake and the patient's biometrical data, which are then used in the determination of the anomalous events and/or of the SUV. Said interface 44 may also be configured as a wired or wireless data interface, and may be even be the same or a similar interface as the input 41.

The input 41 may further be configured to obtain event data, e.g. from one or more additional sensors 60, 61, including the time of the one or more events. These event data are then used by said anomalous event determination unit 42 is configured to use the time of the one or more events in determining the anomalous event information.

Preferably, the device 40 further comprises a synchronization unit 45 for time synchronization of the device with the one or more wearable devices 20 and/or the one or more biometrical data acquisition units 30, 31. In an embodiment, the synchronization unit 45 generates a system clock which is provided to the one or more wearable devices 20 and/or the one or more biometrical data acquisition units 30, 31, in particular to all other components of the system 1, i.e. the synchronization unit 45 takes over the task of the system's synchronization device 90, which can thus be omitted.

Figure 3:
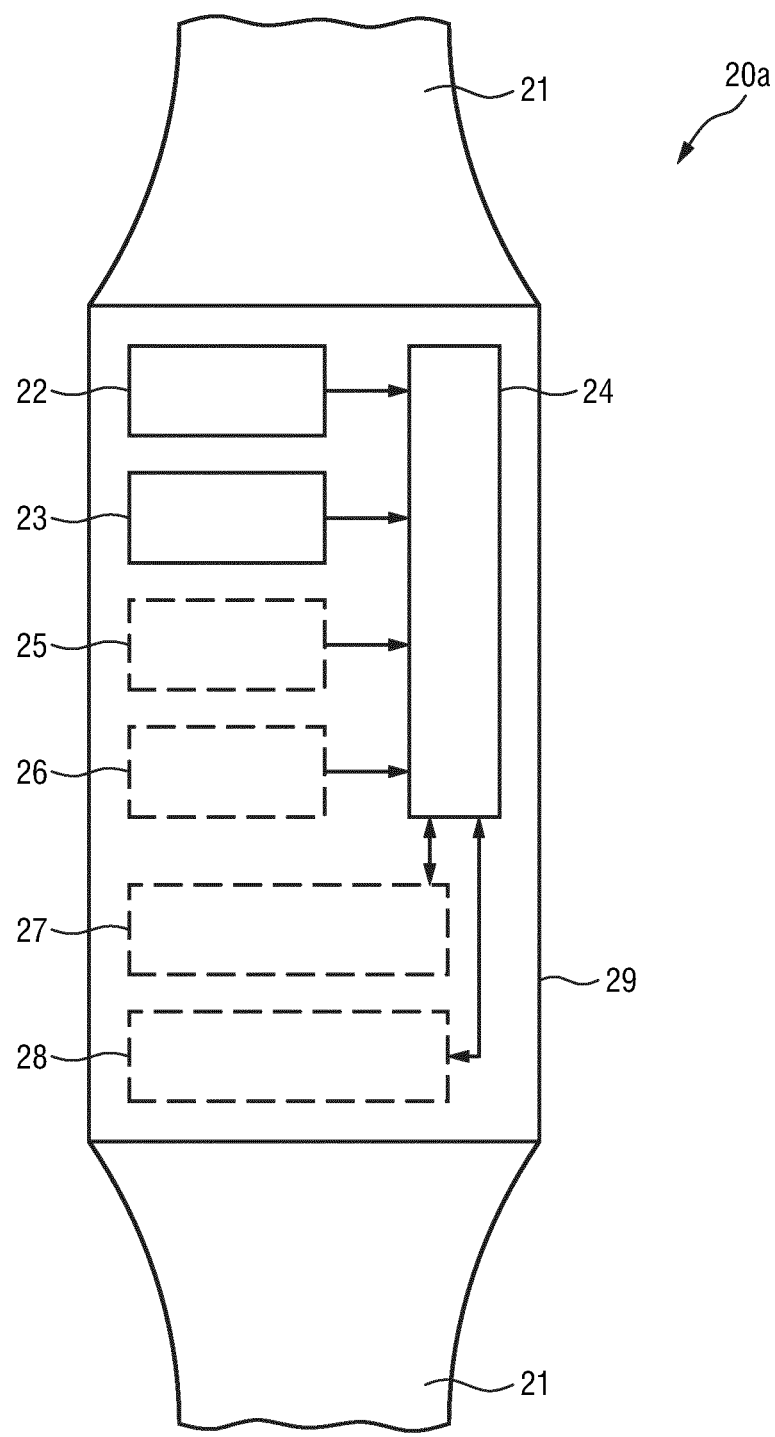
FIG. 3 shows a schematic diagram of a first embodiment of a wearable device according to the present invention.

FIG. 3 shows a schematic diagram of a first embodiment of a wearable device 20a according to the present invention. It comprises a holding element 21 for holding the wearable device at the patient's body. The holding element 21 may e.g. be a wristband for wearing the wearable device 20a like a wristwatch, in which case the wearable device 20a preferably has the form of a wristwatch. In other embodiment the holding element 21 may include a belt, chain, sticker, etc. for mounting the wearable device 20a in some way to the patient's body.

The wearable device 20a further comprises one or more sensing elements 22, 23 for sensing SUV-related data required for the SUV determination. Said SUV-related data include at least the time of a radiotracer uptake by the patient, but preferably includes further data as will be explained below. Further, the one or more sensing elements 22, 23 are configured to sense event data relating to one or more events that may affect the SUV determination. These event data may e.g. comprise movement data and/or activity data reflecting movements and/or activities of the patient, preferably including not only the kind of movement/activity, but also the location, the time, the intensity, and/or the duration. The sensing elements 22, 23 may e.g. include one or more of a motion sensor, an accelerometer, a position detection sensor, a vital sign sensor, a gamma radiation sensor and a camera.

An output 24 is provided for outputting the sensed SUV-related data and event data. Said output 24 may e.g. be implemented as a data interface for wired or wireless output of data, which is able to exchange data with the input 41 of the SUV determination device 40.

The wearable device 20a may further comprise a time measurement unit 25 for recording the time of occurrence of the one or more events sensed as event data, and the output 24 may be configured to output the event data together with the time of occurrence of the related event.

The wearable device 20a may further comprise a synchronization unit 26 for time synchronization of the wearable device 20a with the device 40 for SUV determination, in particular based on a provided system clock, which may e.g. be provided by the synchronization device 90 of the system 1 or the synchronization unit 45 of the device 40.

Further, the wearable device 20a may comprise a user interface 27 enabling input and/or output of user information. This enables a user, in particular the patient, to input SUV-related data, event data and/or biometrical data, e.g. input some personal data or press a button if a predetermined event happens, etc. Further, the patient may be informed or instructed via the user interface 27, e.g. to perform a certain activity, go to a certain location, etc. The user interface 27 may e.g. be implemented as a display, keyboard, touch-screen, etc.

Still further, the wearable device 20a may comprise a communication unit 28 for electronically exchanging data with one or more biometrical data acquisition units 30, 31 and/or with other components of the system 1, in particular via the output 24.

The elements 22 to 28 of the wearable device 20a are preferably arranged in a housing 29 to which the holding element 21 is preferably mounted.

In order to know if an event is affecting the SUV determination (and how much it affects it), certain events that are generally known to directly affect the SUV result can be tracked (like for example if the uptake period is within 50-70 minutes, or if the weight was previously measured or not). For this purpose, the device 40 may be loaded with an imaging protocol that defines the correct time order of the events or the accepted ranges for a given measurement. If that protocol is not being followed, the conclusions taken from the outcome SUV are somehow compromised and in that case and if possible should be accounted for.

For instance, as a first example, for a first scan the patient has to be scanned within 55 to 75 minutes after injection (uptake period from 55 to 75 minutes), with the ideal value being 60 minutes. A second examination of the same patient (e.g. a follow up PET exam for instance after some therapy), the uptake period has to be equal to the first ±10 minutes as target according to the protocol. Deviations are allowed up to maximum ±15 minutes. The wearable device knows if the patient is making a first PET or a follow up examination and is recording the different time events. Every time that this uptake period is not respected, the device has to provide a warning to the technologists. Other protocols may define different target and acceptable uptake periods. The settings of the wearable device depend on the protocol being followed by each specific clinical service.

In a second example the measurement of the local radioactivity in the patient arm by the wearable device via the on-board gamma radiation sensor as function of time can also provide an indication of occurrence of paraveneous administration of the tracer. In case of a paraveneous injection, the gamma radiation sensor will provide a response that would have a very slow decay allowing to warn the clinical staff that the injection was not fully successful and some tracer will be trapped at the injection site, e.g. at the patient arm. In that case such an occurrence has to be registered to be accounted for during the image analysis.

In a third example the muscular activity during the uptake period may be considered. In order to minimize muscular activation that led to unwanted radiotracer accumulation in healthy tissue, the patient is instructed to be in silence and minimum movement during the uptake period. Patterns of motion during that period of time can be logged by the wearable device through a sensor. During the patient image analysis, clinicians can determine if abnormal movement has taken place that could have introduced abnormal radiotracer accumulation in certain body regions that are uncorrelated with the tumor or lesion under examination.

In a fourth example plasma glucose competes with 18F-FDG (the most used radiotracer in PET imaging) for transport into the cells and phosphorylation by hexokinase may be considered. The FDG uptake will be inversely related to the plasma glucose concentration. Thus, the serum glucose concentration at the time of FDG injection has to be obtained. Glucose portable systems connected to the wearable device via a wireless link can be used to record the amount of glucose at that time once again avoiding that way the potential transcription errors. If the serum glucose is high, there may be an increase in false negative findings in oncological PET imaging.

Some protocols like the Uniform Protocols for Imaging in Clinical Trials (UPICT) (18)F-FDG PET/CT protocol (which can currently be found at http://jnm.snmjournals.org/content/56/6/955.long) define certain events that need to happen within a specific time line, as well as target ranges for measurements or patient conditions. Outside those timelines and/or ranges the imaging acquired cannot be taken in full confidence, meaning that conclusions drawn from the outcome SUV can be biased, for example the discussion above in respect to the maximum and minimum allowed uptake period. In case of the paraveneous injection, the UPICT protocol also classifies it in different scenarios (minor, moderate and severe). Images obtained with moderate to severe scenarios should not be used for therapy response assessment unless a correction is derived based on the amount of estimated paraveneous injection. The amount of radiotracer activity trap in the paraveneous injection site can be used to correct the Total Injected Activity in the SUV formula described herein if correctly estimated before the examination.

UPICT also defines the allowed levels of plasma glucose at the time of the injection. For non-diabetic patients concentrations above 200 mg/dL require that the scan is rescheduled, between 150 and 200 mg/dL the referring physician has to be consulted. Values below 150 mg/dl are considered acceptable.

The determination of the SUV may be performed as follows. A reconstructed image (e.g. a PET image) is a 3D volume composed of L×M×N voxels. L, M and N might be equal or differ depending on the image acquisition protocol. Typically each voxel has between 1×1×1 mm3 to 4×4×4 mm³. The SUV for each voxel is given by the following expression:

$$SUV = \frac{\text{Reconstructed Activity in Patient Tissue}}{\text{Total Injected Activity} \times \text{Patient Weight}}$$

where Reconstructed Activity in Patient Tissue is the radioactivity activity concentration [kBq/ml] measured by the PET scanner within a region of interest (ROI), the Total Injected Activity is the decay-corrected amount of injected radiolabeled FDG [kBq], and the Patient Weight is the weight of the patient [g] measured on the day of the PET exam, which is used as a normalization factor.

There are other normalization factors beside the Patient Weight for the SUV such as the "Lean Body Mass" and the "Body Surface Area". To estimate the Lean body Mass and the Body Surface Area besides the weight the height if each patient is also measured before the beginning of the PET scan.

In order to maximize the uptake of the tracer in the tumor and to minimize the uptake in the healthy tissues, the patient has to rest between 50 and 70 minutes right after the tracer injection at $T_0$, before the actual PET scan start at $T_1$. Due to the exponential decay of the radiotracer, the Reconstructed Activity in Patient Tissue has to be corrected by a factor that is given by $e^{\Delta T/\tau}$, in which $\tau$ is the half-life of the radiotracer (for the most widely used radiotracer, 18F-FDG, in PET this is of about 110 minutes) and $\Delta T = T_1 - T_0$.

The data obtained by the wearable device can provide direct information on the time of injection $T_0$ while the imaging system provides the reconstructed activity at time $T_1$. Both pieces of information are used to compute the reconstructed activity corrected by the radiotracer uptake period $\Delta T = T_1 - T_0$. Also the wearable device can collect from a wireless weight scale information on the Patient Weight, avoiding for instance transcription errors that can directly affect the accuracy of the SUV outcome. In a possible embodiment the wearable device can also collect from an automated dose injector via a wireless communication channel the Total Injected Activity and the time of injection $T_0$. In an alternative embodiment the technologists or clinical staff types in the wearable user interface the injected amount right after the injection and not only some time later.

Certain events like for example the toilette 30 minute after uptake should be recorded in order to confirm that the patient has complied with imaging protocol. They do not directly enter into the SUV computation formula, but are certain tasks that guarantee that the reconstructed imaging are not affected by physiological radiotracer background that can hide the presence of a tumor. Flushing the bladder is needed in order to prevent background activity that compromises the reconstructed activity in the patient issue. Motion and anxiety level of the patient during the 50-70 minutes uptake period must be recorded since it will increase the uptake in the healthy muscle affecting of course the overall uptake in the tumor region. This is why the wearable device may be equipped with a motion sensor and rise alarms to the technologists.

Figure 4:
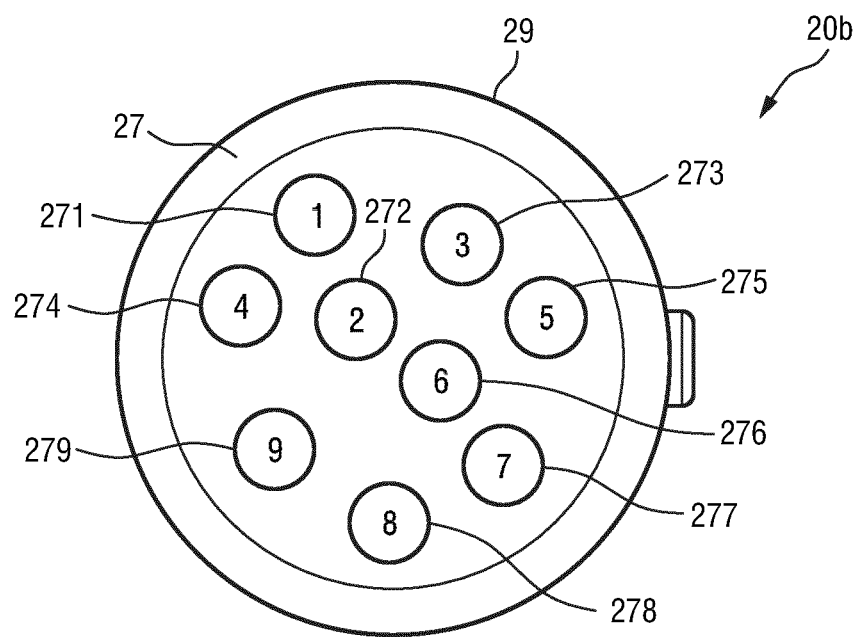
FIG. 4 shows a front view of a second embodiment of a wearable device according to the present invention.

FIG. 4 shows a front view of a second embodiment of a wearable device 20b according to the present invention, which will be explained in the following in the context of the particular use scenario. The wearable device 20b is configured as a wrist-worn device (the holding element is not shown, but may be same as for the wearable device 20a). FIG. 4 particularly shows a housing 29 around a user interface 27 in the form of a touchscreen showing a plurality of buttons that may be actuated by the patient for entering information, e.g. the time of predetermined events or for prompting predetermined actions.

The buttons on the user interface 27 may e.g. include
a button 271 for registration of the patient intake (i.e. the intake of the patient in the NM department; for instance, when the patient gets the wearable device and a button is pushed to signal that the intake in the NM department has been made);
a button 272 for registration of the injection time;
a button 273 for registration of the patient entering the resting area;
a button 274 for registration of the patient leaving the resting area;
a button 275 for registration of the patient being in the rest rooms;
a button 276 for registration of the start of an imaging examination (e.g. PET examination);
a button 277 for registration of the end of an imaging examination
a button 278 for registration of the discharge of the patient; and
a button 279 for initiating a support call.

Other, more or less buttons for other events can be foreseen as well.

As explained above, in use, the wearable device 20b is attached to the patient and is able to establish a (preferably bi-directional) communication link, e.g. via NFC, Wi-Fi, Bluetooth or an equivalent wireless link with a central station. A GPS or equivalent indoor positioning receiver may also be included. Other biometrical data acquisitions means, like bio-sensors, accelerometers, etc., in particular for motion detection, may be included as well. Further, an on-board gamma radiation dosimeter might as well be included in order to provide real-time and the reference value for the gamma radiation dose received by the patient during the examination.

Further, the wearable device 20b is preferably synchronized with a central station and is loaded with a software application ('app') that includes one button for each of the clinical procedures relevant for the imaging procedure, e.g. relevant for PET quantification. The app may register the time for each of the clinical events and associated information (for example, patient weight or injected dose, etc.).

Anomalous events can also be recorded with the wearable device 20b, like for example patient movement in the resting room prior to the examination (e.g. a PET examination) using the on-board positioning receiver or physiological events, like motor stress, that can impair an adequate radiotracer uptake.

A central station, such as the synchronization device 90 shown in FIG. 1, or the SUV determination device 50, may generate a reference system clock. The clock is wirelessly distributed to the wearable device 20b and either by a wired or wireless connection to the other components of the system as explained above (e.g. to the place of patient injection or automatic injector/dispenser, PET data acquisition system, PET exam console).

A stream of the different clinical or anomalous events together with the time of occurrence may be generated by the wearable device 20b, which is transmitted to the SUV determination device 40 and stored in a database, preferably with a link to the patient examination. It has been found that the time at which SUV-related events occur play an important role in the determination of the SUV. For instance, in an exemplary situation, although the target uptake period is 60 minutes, due to the service workload it was not possible to take the patient to the imaging scanner earlier said 75 minutes. However, and because that is not done in the clinical routine, the technologist had not registered the exact hour of the beginning of the uptake period and just assumes 60 minutes neglecting the 15 minutes extra. In that case the introduced error in the SUV determination would be almost 15% having a direct impact of the SUV outcome measured in the image analysis phase after the exam. That can mislead the image interpretation by the medical doctor since that is no longer doing a quantitative assessment of the SUV that might choose a different type of treatment for that patient.

Figure 5:
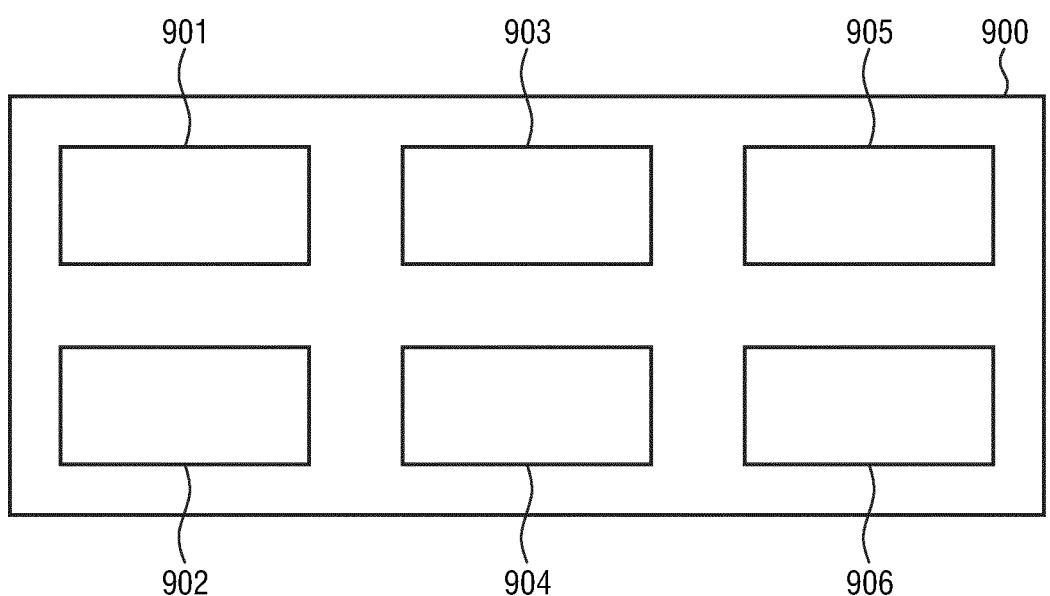
FIG. 5 shows a schematic diagram of an embodiment of a master clock generator and exam logger for use in a system according to the present invention.

In a particular architecture of the system 1 a central role may be taken by the synchronization device 90, which may also be called master clock generator and exam logger, i.e. which may not only generate and distribute a synchronization time, but may also log events. A schematic diagram of a generic implementation of such a master clock generator and exam logger 900 is shown in FIG. 5. Different hardware implementations are possible, either using a full fledge computer of a dedicated hardware running FPGA or an equivalent processor 901. This device 900 receives from the external world a clock signal. Correct synchronization can be achieved using e.g. the Consistent Time Integration Profile as defined in the IHE IT Infrastructure Technical Framework. The Consistent Time Profile requires the use of the Network Time Protocol (NTP) (as defined at www.NTP.org).

Besides auxiliary units related to on-board power distribution (unit 902), memory and local mass storage (unit 903) for temporary storage of clinical events, the device 900 has several LAN physical interfaces 904 (wither copper or fiber) to interconnect to the dose calibrator 70 (for dose calibrators which have also a LAN interface), to a dose injector dispenser/automatic perfusion 80 (if available), biometrical data acquisition units 30, 31 and to the imaging device 10. The LAN link is used to further re-distribute the synchronization clocks as well as the associated time of a particular clinical event. The device 900 further comprises a wireless hardware unit 905 in order to keep communication with the wearable device used by the patient and a memory 906 for storing e.g. the processing software.

According to an embodiment of the present invention for solving the problems described above (and related other problems) use is made of a mobile patient tracking device (generally called wearable device herein, but also called NM-Tracker or NMT), equipped with a unique assembly of sensors tailored to support the NM workflow specific data logging and communication tasks. The wearable device is assigned and handed out to the patient (e.g. during its registration procedure), and accompanies him/her until he/she leaves the department again. It offers a simple user interface to display procedure related information to the patient. Using the inbuilt gamma radiation sensor, the device automatically detects a radiotracer injection event. Further workflow related information may be captured during the procedure via a (near-field) RF-interface and/or an inbuilt camera (e.g. in combination with QR-tag or OCR technology). Via e.g. the existing wireless network in the clinic, the device communicates with a central SUV determination device to transfer collected path (motion) tracking information and recorded technical and physiological parameters). An application running on the SUV determination device analyzes the incoming data, checks for workflow state consistency, raises warnings to the medical staff in case of any undesirable events. It furthermore offers an interface to submit further information to the remotely connected wearable devices.

The wearable device may be designed in such a way that it hampers obvious possibilities of accidental misuse. As an example, in order to avoid that patients leave the device with accompanying relatives e.g. when they visit the bathroom, it should be attached to the patient in a non-obstructive way. A possible design supporting this could be in form of a (smart) wristwatch. Furthermore its design should consider special clinical requirements regarding sterilization, etc.

An embodiment of the wearable device comprises a tailored display to pass information to the patient, a simple way to allow the patient to provide feedback (e.g. to remotely confirm a new schedule), a wireless two-way communication interface (802.11x, Bluetooth, . . . ), a inbuilt digital camera, a 3D-acceleration sensor, a gamma radiation sensor, a data processing unit and an interface to wirelessly re-charge the internal batteries (e.g. via Qi-Technology). The gamma radiation sensor module (realized e.g. in FGMOS-FET technology) may be designed to reliably detect gamma radiation for standard NM isotope particle energies. It preferably provides a higher sensitivity in one spatial direction. If attached to the patient, the preferred direction is towards the body.

In the following, exemplary use-scenarios for the wearable device are described along with additional technical information:

The wearable device may be centrally stored and re-charged, e.g. at the patient registration desk. During charging, the wearable device's internal clock is synchronized with a central clock unit. Data not yet transferred to the SUV determination device 40 (sometimes also called NMT server or NMT base station) are securely uploaded during this time and finally deleted from the device.

When put off the charging station, the wearable device may automatically set to active mode and expects to be assigned to a new patient. The assignment can be performed e.g. via putting a patient record QR-/bar-code in front of the wearable device's camera. After identifying a valid patient ID tag, the device switches to a state-machine controlled tracking mode (displayed at the wearable device e.g. via a color change) according to the examination specific workflow steps.

Patient movement through the clinical area may be recorded via information of the motion sensors and/or the analysis of the signal strength from multiple WLAN access points. The information is frequently automatically uploaded to the SUV determination device for further evaluation. In order to account for special data security/privacy requirements in a clinical environment, all exchanged data are encrypted. Automatic motion pattern analysis is applied to make the staff aware of patients requiring further assistance and guidance to optimize the examination result. The medical staff can also directly access additional related information via the SUV determination device, e.g. whether and when the patient last visited the bathroom. Furthermore, the motion detection can be used to directly provide location guidance to patients in order to help them to find their way through large departments.

In case of a scheduling delay, not yet prepared/injected patients may receive new scheduling information via the display. This allows them to leave the waiting area and e.g. visit the clinic's recreation zone. An interaction (e.g. confirmation) request might be additionally indicated via a special visual signal (e.g. a blinking of the wearable device).

When entering a new workflow position/step, additional parameters may be stored and transferred via the wearable device. For instance, when the injection is prepared, the syringe comes with (e.g. a printed) QR-tag containing related radiotracer type and calibration (e.g. timestamp, amount) information. Recognizing the QR-code via the wearable device's camera activates the internal gamma radiation sensor. The wearable device, distally attached to the patient from where the radiotracer enters the body (e.g. worn at the left wrist, when injecting into the right medial cubital vein), immediately detects the radiotracer bolus and logs the event together with the timestamp. The data transferred to the SUV determination device 40 enable the application there to determine a study optimal image acquisition schedule. Adding the dwell-counter determined remaining tracer-activity in the syringe, the SUV determination device 40 exactly knows all the parameters to calculate what amount of tracer has been administered to the patient at what point in time.

Start and duration of the subsequent image acquisition can be logged (e.g. via detecting typical orientation and movement patterns during the couch positioning, eventually in combination with detecting the additional gamma radiation dose during the anatomical/scouting scan e.g. on PET/CT, SPECT/CT scanner combinations).

After completing the workflow, the clinician may check during the debriefing with the patient whether all relevant patient information for subsequent quantitative data analysis has been transferred to the SUV determination device 40. This might be indicated e.g. via a specific color code of the device. If that is not the case he/she takes care of finalizing this step, before the patient is sent home.

When leaving the department, the patient returns the wearable device to the reception desk where again the device status is checked again and the device prepared for cleaning/recharging.

In accordance with the above disclosure, various examples are described below:

EXAMPLE 1

Device for standard uptake value, SUV, determination in emission tomography, said device comprising:

an input 41 for obtaining, from one or more wearable devices 20, 20a, 20b and/or one or more biometrical data acquisition units 30, 31, SUV-related data required for SUV determination including the time of a radiotracer uptake by a patient, and for obtaining event data relating to one or more events that may affect the SUV determination, an anomalous event determination unit 42 for determining from the obtained event data anomalous event information indicating one or more anomalous events that affect the SUV determination, and an SUV determination unit 43 for determining the SUV from said SUV-related data taking into account the anomalous event information.

EXAMPLE 2

Device as in Example 1, wherein said SUV determination unit 43 is configured to determine the SUV from SUV-related data including the radiotracer activity concentration in the patient's tissue, the administered dose of the radiotracer uptake and the patient's biometrical data, in particular the patient's weight, height and/or total surface area.

EXAMPLE 3

Device as in Example 1, further comprising an interface 44 for interconnecting with a radiotracer dose calibrator, a radiotracer dose injector, one or more biometrical data acquisition units, in particular a weighting scale, a height measuring scale, a blood pressure meter, and/or a blood glucose analyzer, and/or an imaging arrangement to obtain one or more pieces of SUV-related data including the radiotracer activity concentration of the patient's tissue, the administered dose of the radiotracer uptake and the patient's biometrical data.

EXAMPLE 4

Device as in Example 1, wherein said input 41 is further configured to obtain event data including the time of the one or more events and said anomalous event determination unit 42 is configured to use the time of the one or more events in determining the anomalous event information.

EXAMPLE 5

Device as in Example 1, further comprising a synchronization unit 45 for time synchronization of the device with the one or more wearable devices and/or the one or more biometrical data acquisition units, in particular for generating a system clock provided to the one or more wearable devices and/or the one or more biometrical data acquisition units.

EXAMPLE 6

Method for standard uptake value, SUV, determination in emission tomography, said method comprising:

obtaining, from one or more wearable devices 20, 20a, 20b and/or one or more biometrical data acquisition units 30, 31, SUV-related data required for SUV determination including the time of a radiotracer uptake by a patient, and for obtaining event data relating to one or more events that may affect the SUV determination, determining from the obtained event data anomalous event information indicating one or more anomalous events that affect the SUV determination, and determining the SUV from said SUV-related data taking into account the anomalous event information.

EXAMPLE 7

Wearable device configured to be worn by a patient, said wearable device comprising:

a holding element 21 for holding the wearable device at the patient's body, one or more sensing elements 22, 23 for sensing standard uptake value, SUV, related data required for SUV determination in emission tomography, including the time of a radiotracer uptake by the patient, and event data relating to one or more events that may affect the SUV determination, and an output 24 for outputting the sensed SUV related data and event data.

EXAMPLE 8

Wearable device as in Example 7,
wherein said sensing elements include one or more of a motion sensor, an accelerometer, a position detection sensor, a vital sign sensor, a radiation sensor and a camera.

EXAMPLE 9

Wearable device as in Example 7,
further comprising a time measurement unit 25 for recording the time of occurrence of the one or more events sensed as event data,
wherein said output 24 is configured to output the event data together with the time of occurrence of the related event.

EXAMPLE 10

Wearable device as in Example 7,
further comprising a synchronization unit 26 for time synchronization of the wearable device with a device for SUV determination as in Example 1, in particular based on a provided system clock.

EXAMPLE 11

Wearable device as in Example 7,
further comprising a user interface 27 enabling input and/or output of user information.

EXAMPLE 12

Wearable device as in Example 7,
further comprising a communication unit 28 for electronically exchanging data with one or more biometrical data acquisition units 30, 31.

EXAMPLE 13

Emission tomography system, in particular particle emission tomography, PET or single-photon emission computed tomography, SPECT, system, said system comprising:

an imaging arrangement 10 for acquiring image data of a patient, one or more wearable devices 20, 20a, 20b as in Example 7 configured to be worn by the patient, one or more biometrical data acquisition units 30, 31 for acquiring biometrical data, in particular a weighting scale, a height measuring scale, a blood pressure meter, and/or a blood glucose analyzer, and for providing said biometrical data to one or more wearable devices.

a device 40 for standard uptake value, SUV, determination as in Example 1 from SUV related data and event data obtained from the one or more wearable devices and/or the one or more biometrical data acquisition units, and an evaluation unit 50 for evaluating the acquired image data using the determined SUV.

EXAMPLE 14

System as in Example 13,
further comprising one or more additional sensors 60, 61 for sensing one or more event data, wherein said device 40 for SUV determination is configured to additionally use the one or more event data sensed by one or more additional sensors 60, 61 in the SUV determination.

EXAMPLE 15

Computer program comprising program code means for causing a computer to carry out the steps of the method as in Example 6 when said computer program is carried out on the computer.

According to another embodiment of the invention described with reference to FIG. 2, a device 40 for standard uptake value, SUV, determination during an emission tomography imaging procedure of a patient to which a radiotracer dose has been administered at an imaging facility, is disclosed. The emission tomography imaging procedure may for example be a PET or a SPECT imaging procedure. The device 40 includes at least one input 41, 44 that is configured to receive SUV-related data required for SUV determination and event data relating to one or more events that may affect the SUV determination. The SUV-related data may include one or more of the following: a time of administration of the radiotracer dose to the patient; a radiotracer dose administered to the patient; a radiotracer activity concentration in a region within the patient; the patient's weight; the patient's height; the patient's total surface area, calibration data indicative of a residual activity in a syringe after administration the radiotracer dose to the patient. One or more of these SUV-related data may be used in the computation of an SUV from the emission tomography imaging procedure as described above in relation to the SUV equation. The present invention recognizes that one or more events, herein described as event data, may affect the accuracy of the so-computed SUV. Accordingly, the event data received by the at least one input 41, 44 of the device 40 may include at least one of: i) a time at which an emission tomography imaging procedure of the patient is performed; ii) patient motion data indicative of the patient's motion during the period between administration of the radiotracer dose and a start of the emission tomography imaging procedure; iii) patient position data indicative of the patient's position within the imaging facility during the period between administration of the radiotracer dose and a start of the emission tomography imaging procedure; iv) patient vital signs data indicative of the patient's vital signs during the period between administration of the radiotracer dose and a start of the emission tomography imaging procedure. With respect to i) if the start of the imaging procedure is not started, or indeed completed, within a predetermined time after the administration of the radiotracer dose, errors can occur in the calculated SUV due to the decaying nature of the dose. However, these maybe corrected-for as described below. With respect to ii) patient motion during the so-called uptake period between administration of the radiotracer dose and the measurement of its distribution during the tomographic imaging procedure can likewise affect the calculated SUV. For example, excessive exercise during this period may affect metabolism of the radiotracer and its distribution. Again, these maybe corrected-for as described below. With respect to iii) patient position data that, for example, indicates whether the patient is resting in a desired room, or making trips to the bathroom, or is indeed elsewhere in a hospital or imaging facility can also affect the calculated SUV. Again, as described below, such data may be used to correct the SUV as described below. With respect to iv) patient vital signs during the uptake period, e.g. one or more of patient heart rate sensor, body temperature, respiration, blood pressure, skin conductivity, blood oxygenation i.e. SPO2, blood glucose, may also be indicative of errors in the calculated SUV. For example when any of these data lie outside a predetermined range and error may be expected due to e.g. excessive exercise during the uptake period. Again, these maybe corrected-for as described below. The device 40 also includes an anomalous event determination unit 42 that is configured to determine, based on one or more of the above event data, anomalous event information indicative of one or more anomalous events that affect the SUV determination. As outlined above the anomalous event determination unit assesses the relevant data, compares this to an expected range, or expected data, and, where necessary flags that an anomaly has occurred. Moreover, the device 40 includes an SUV determination unit 43 that is configured to determine the SUV based on said SUV-related data taking into account the anomalous event information. With respect to i), for example the imaging duration can be extended or shortened, or correction factors may be applied to the calculated SUV. With respect to ii), iii) and iv), for example correction factors may be applied to the SUV that take account of excessive exercise, or the start time or duration of the tomographic imaging procedure may be amended from a standard value. Advantageously, rather than simply abandoning and re-scheduling the radiotracer uptake and tomographic imaging procedure, the device of the present invention allows for the computation of an accurate SUV by compensating for the various described anomalous events.

According to another embodiment of the invention described with reference to FIGS. 2, 3, and 4, a method of SUV determination is disclosed. The method may be used in emission tomography during an emission tomography imaging procedure of a patient to which a radiotracer dose has been administered at an imaging facility. The method comprises the steps of: a) obtaining SUV-related data required for SUV determination, b) obtaining event data relating to one or more events that may affect the SUV determination, c) determining based on the obtained event data anomalous event information indicating one or more anomalous events that affect the SUV determination, and d) determining the SUV based on said SUV-related data taking into account the anomalous event information. The SUV-related data and event data may be as described in the previous embodiment. The above method steps may be stored as instructions or program code in a computer-readable format. Moreover the method steps may be carried-out by a computer.

According to another embodiment of the invention described with reference to FIG. 2 and FIG. 3 a wearable device 20, 20a, 20b is disclosed. The wearable device may be used for standard uptake value, SUV, determination during an emission tomography imaging procedure of a patient to which a radiotracer dose has been administered at an imaging facility. The wearable device comprises a holding element 21, for example a strap, a belt or a necklace, for holding the wearable device at the patient's body; and one or more sensing elements 22, 23 for sensing SUV-related data required for SUV determination in emission tomography. The sensed SUV-related data may be one or more of the above data described in relation to the previous embodiment. Preferably said SUV-related data includes at least a time of administration of the radiotracer dose to the patient. Moreover the wearable device includes an output 24 for outputting the sensed SUV-related data. In the preferred configuration the one or more sensing elements 22, 23 for sensing the time of administration of the radiotracer dose to the patient includes at least one of a) a wireless sensor configured to wirelessly receive the time at which a radiotracer dose injector 80 administers the radiotracer dose to the patient; and b) a gamma radiation sensor arranged such that when the wearable device is worn by the patient the radiation sensor senses gamma radiation emitted from the patient's body; the gamma radiation sensor being further configured to provide a timestamp indicative of the time at which the sensed gamma radiation meets a predetermined threshold condition. The wireless sensor thus provides on-patient SUV-related data storage that can be later read-out, for example by the device 40, and used to determine a SUV for a region within a patient. The wireless sensor provides automated data transfer, thereby reducing the chance of human errors, as compared to a manually-recorded time of dose administration. Moreover, because the data is acquired by the wearable device it is inherently patient-specific, the chance of mixing-up patient data is reduced. In one configuration the gamma radiation sensor (b) may be used on its own to monitor the post-injection influx of the radiotracer to the patient, for example from a vein or artery or other in-body region of the patient such as a limb, i.e. the wrist or leg, and thereby provide a time at which the dose was administered to the patient. This may be used to validate a manually-recorded time of injection, or to provide the actual time of injection. In another configuration the gamma radiation sensor (b) may be used in combination with the wireless sensor (a) in order to confirm the time of automated dose injection, and to identify, for example that a radiotracer was actually injected into the patient at all. Wireless RF as used in e.g. Near Field Communication, RFID, and Bluetooth may be for example used for this purpose although these specific implementations should not be seen as limiting. Indeed any wireless transmitter-receiver system may be used to transfer the desired data, including RF, infrared, ultrasound and optical communication. In this embodiment the wireless sensor may also be used receive additional SUV-related data as described above. This may be received wirelessly from wireless-transmitting systems. These include for example the radiotracer dose administered to the patient, or radiotracer dose calibration data indicative of a residual activity in a syringe after administration the radiotracer dose to the patient, either of which may be received e.g. from radiotracer dose injector 80, the patient's weight, which may be received from a wireless patient weighing scale, and the patient's height or surface area that may be received from a wireless height measurement system, or a computer system configured to determine the patient's surface area based on a model having, as input, the patient height and weight. In this embodiment the wireless sensor may additionally be used to receive, and to store, event data relating to one or more events that may affect the SUV determination. The event data is described above, and may be received wirelessly from one or more sensors, or be sensed directly by a sensor that forms part of the wearable device. Such sensors include an accelerometer, a patient position sensor, a patient vital signs sensor selected from the group: a heart rate sensor, a body temperature sensor, a respiration sensor, a blood pressure sensor, a skin conductivity sensor, an SPO2 sensor, a blood glucose sensor. Advantageously the so-defined wearable device 20, 20a, 20b may be used to collect and store various SUV-related data and/or various event data which can serve as input to the device 40 for use in providing an SUV for the patient. Optionally the wearable device 20, 20a, 20b may include a time measurement unit 25 for recording the time of measurement of the corresponding event data; this being configured to output the time of measurement of the event data and/or the corresponding event data. Optionally the wearable device 20, 20a, 20b may include a synchronization unit 26 for time synchronization of the wearable device with the device 40 for SUV determination.

According to another embodiment of the invention an imaging arrangement 10 is disclosed. The imaging arrangement 10 comprises an emission tomography imaging system for acquiring image data of a patient, in particular a PET or a SPECT imaging system; one or more wearable devices 20, 20a, 20b as described above in the previous embodiment; and a device 40 for standard uptake value, SUV, determination as describe above. The device 40 is configured to determine an SUV based on the SUV-related data and the event data received by the at least one input 41, 44 of the device 40; and based on at least the SUV-related data outputted by the one or more wearable devices 20, 20a, 20b. Moreover, the device 40 includes an evaluation unit 50 for evaluating the acquired image data using the determined SUV. Optionally the device 40 of the imaging arrangement 10 may also be configured to determine the SUV based further on the event data outputted by the one or more wearable devices 20, 20a, 20b.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for standard uptake value (SUV) determination during an emission tomography imaging procedure of a patient to which a radiotracer dose has been administered for providing image data by an emission tomography imager at an imaging facility, the device comprising:
   at least one input configured to receive SUV-related data required for SUV determination and event data relating to one or more events that affecting the SUV determination,
   wherein the SUV-related data includes at least a time of administration of the radiotracer dose to the patient, and
   wherein the event data includes at least one of:
      a time at which an emission tomography imaging procedure of the patient is performed by the emission tomography imager,
      patient movement and activity data indicative of physical movement and activity of the patient within the imaging facility during a period between the administration of the radiotracer dose and a start of the emission tomography imaging procedure,
      patient location data indicative of a location of the patient within the imaging facility during the period between the administration of the radiotracer dose and the start of the emission tomography imaging procedure, or
      patient vital signs data indicative of vital signs of the patient during the period between administration of the radiotracer dose and the start of the emission tomography imaging procedure;
   an anomalous event determination unit configured to determine, based on the event data, anomalous event information indicative of one or more anomalous events that affect the SUV determination; and
   an SUV determination unit configured to determine the SUV based on the SUV-related data taking into account the anomalous event information.

2. The device as claimed in claim 1 wherein the SUV-related data further includes at least one of:
   a radiotracer dose administered to the patient;
   a radiotracer activity concentration in a region within the patient;
   a weight of the patient;
   a height of the patient; or
   a total surface area of the patient.

3. The device as claimed in claim 1, wherein the at least one input is configured to receive at least one of the following data from one or more patient-wearable devices:
   the time of administration of the radiotracer dose to the patient;
   the time at which an emission tomography imaging procedure of the patient is performed;
   the radiotracer dose administered to the patient;
   the patient movement and activity data indicative of the physical movement and activity of the patient within the imaging facility during the period between administration of the radiotracer dose and a start of the emission tomography imaging procedure;
   the patient location data indicative of the location of the patient within the imaging facility during the period between administration of the radiotracer dose and the start of the emission tomography imaging procedure;
   the patient vital signs data indicative of the vital signs of the patient during the period between administration of the radiotracer dose and a start of the emission tomography imaging procedure.

4. The device as claimed in claim 1, wherein the SUV-related data received at least one input further includes radiotracer dose calibration data indicative of a residual activity in a syringe after administration the radiotracer dose to the patient.

5. The device as claimed in claim 3 further comprising a synchronization unit for time synchronization of the device with the one or more patient-wearable devices.

6. A method of determining standard uptake value (SUV) during an emission tomography imaging procedure of a patient to which a radiotracer dose has been administered for providing image data by an emission tomography imager at an imaging facility, the method comprising:

obtaining SUV-related data required for SUV determination, wherein the SUV-related data includes at least a time of administration of the radiotracer dose to the patient;

obtaining event data relating to one or more events able to affect the SUV determination, wherein the event data includes at least one of:
- a time at which an emission tomography imaging procedure of the patient is performed by the emission tomography imager;
- patient movement and activity data indicative of physical movement and activity of the patient within the imaging facility during a period between the administration of the radiotracer dose and a start of the emission tomography imaging procedure; or
- patient location data indicative of a location of the patient within the imaging facility during the period between the administration of the radiotracer and the start of the emission tomography imaging procedure;

determining based on the obtained event data anomalous event information indicating one or more anomalous events that affect the SUV determination; and determining the SUV based on the SUV-related data taking into account the anomalous event information.

7. The method according to claim 6 wherein the SUV-related data further includes:
- a radiotracer dose administered to the patient;
- a radiotracer activity concentration in a region within the patient;
- a weight of the patient;
- height of the patient; and
- a total surface area of the patient.

8. A non-transitory computer readable medium having stored thereon software instructions that, when executed by a processor, cause the processor to carry out the method as claimed in claim 6.

9. A wearable device for standard uptake value (SUV) determination during an emission tomography imaging procedure of a patient to which a radiotracer dose has been administered for providing image data of the patient by an emission tomography imager at an imaging facility, the wearable device comprising:
- a holding element for holding the wearable device at a body of the patient;
- one or more sensors for sensing SUV-related data required for SUV determination in emission tomography, including at least a time of administration of the radiotracer dose to the patient; and
- an output for outputting the sensed SUV-related data,
wherein the one or more sensors for sensing the time of administration of the radiotracer dose to the patient includes at least one of:
- a wireless sensor configured to wirelessly receive a time at which a radiotracer dose injector administers the radiotracer dose to the patient; and
- a gamma radiation sensor arranged such that, when the wearable device is worn by the patient, the radiation sensor senses gamma radiation emitted from the patient's body, the gamma radiation sensor being further configured to provide a timestamp indicative of the time at which the sensed gamma radiation meets a predetermined threshold condition.

10. The wearable device as claimed in claim 9 wherein the one or more sensing elements for sensing SUV-related data include a wireless sensor configured to wirelessly receive SUV-related data indicative of at least one of:
- the radiotracer dose administered to the patient;
- radiotracer dose calibration data indicative of a residual activity in a syringe after administration the radiotracer dose to the patient;
- a weight of the patient;
- a height of the patient; or
- a surface area of the patient.

11. The wearable device as claimed in claim 9 wherein the one or more sensors are further configured to sense event data relating to one or more events that affect the SUV determination; and wherein said output is further configured to output the event data; and wherein the one or more sensing elements includes at least one of the following:
- an accelerometer, a patient position sensor, a patient vital signs sensor selected from the group: a heart rate sensor, a body temperature sensor, a respiration sensor, a blood pressure sensor, a skin conductivity sensor, an SPO2 sensor, a blood glucose sensor; and/or
- a wireless sensor configured to receive data indicative of at least one of:
- the patient's heart rate, the patient's body temperature, the patient's respiration, the patient's blood pressure, the patient's skin conductivity, the patient's SPO2, the patient's blood glucose, the patient's position in the imaging facility based on camera image data.

12. The wearable device as claimed in claim 9 further comprising a time measurement unit for recording a time of measurement of the corresponding event data; and
wherein said output is configured to output the event data and the time of measurement of the corresponding event data.

13. The wearable device as claimed in claim 9 further comprising a synchronization unit for time synchronization of the wearable device with the device for the SUV determination.

14. An imaging arrangement comprising:
- a particle emission tomography (PET) imaging system or a particle emission tomography (PET) imaging system for acquiring the image data of the patient;
- the wearable device as claimed in claim 9; and
- a device for standard uptake value (SUV) determination, wherein the SUV device is configured to determine the SUV based on the SUV-related data and the event data received by at least one input of the SUV device, and based on at least the SUV-related data outputted by the wearable device; and
- an evaluation unit for evaluating the acquired image data using the determined SUV.

15. The imaging arrangement as claimed in claim 14 wherein the SUV device is further configured to determine the SUV based further on the event data outputted by the one or more wearable devices.

16. The device as claimed in claim 1, wherein the emission tomography imager comprises a particle emission tomography (PET) imaging system or a single-photon emission computed tomography (SPECT) imaging system.

17. The method as claimed in claim 6, wherein the emission tomography imager comprises a particle emission tomography (PET) imaging system or a single-photon emission computed tomography (SPECT) imaging system.

* * * * *